United States Patent
Hamamah et al.

(10) Patent No.: US 9,453,259 B2
(45) Date of Patent: Sep. 27, 2016

(54) METHODS FOR ASSESSING ENDOMETRIAL RECEPTIVITY OF A PATIENT AFTER CONTROLLED OVARIAN HYPERSTIMULATION

(71) Applicants: INSERM (INSTITUT NATIONAL DE LA SANTE ET DE LA RECHERCHE MEDICALE), Paris (FR); UNIVERSITE DE MONTPELLIER 1, Montpellier (FR); Centre Hospitalier Universitaire de Montpellier, Montpellier (FR)

(72) Inventors: Samir Hamamah, Montpellier (FR); Delphine Haouzi, Montpellier (FR)

(73) Assignees: INSERM (INSTITUT NATIONAL DE LA SANTE ET DE LA RECHERCHE MEDICALE), Paris (FR); UNIVERSITE DE MONTPELLIER 1, Montpellier (FR); Centre Hospitalier Universitaire de Montpellier, Montpellier (FR)

( * ) Notice: Subject to any disclaimer, the term of this patent is extended or adjusted under 35 U.S.C. 154(b) by 0 days.

(21) Appl. No.: 14/352,768

(22) PCT Filed: Oct. 22, 2012

(86) PCT No.: PCT/EP2012/070892
§ 371 (c)(1),
(2) Date: Apr. 18, 2014

(87) PCT Pub. No.: WO2013/057316
PCT Pub. Date: Apr. 25, 2013

(65) Prior Publication Data
US 2014/0371092 A1    Dec. 18, 2014

(30) Foreign Application Priority Data
Oct. 21, 2011    (EP) .................... 11306364

(51) Int. Cl.
C12Q 1/68    (2006.01)

(52) U.S. Cl.
CPC .......... *C12Q 1/6876* (2013.01); *C12Q 1/6883* (2013.01); *C12Q 2565/513* (2013.01); *C12Q 2600/158* (2013.01); *C12Q 2600/166* (2013.01)

(58) Field of Classification Search
None
See application file for complete search history.

(56) References Cited

PUBLICATIONS

Haouzi (Human Reproduction vol. 24 No. 6 pp. 1436-1445 2009).*
Hoshikawa et al (Physical Genomics 2003 vol. 12 pp. 209-219).*
Chan (G&P magazine 2006 vol. 6 No. 3 pp. 20-26).*
Roman-Roman (Bone 2003 vol. 32 pp. 474-482).*
Haouzi et al., "Gene expression profile of human endometrial receptivity: comparison between natural and stimulated cycles for the same patients", Human Reproduction, 2009, pp. 1436-1445, vol. 24, No. 6.
Haouzi et al., "Controlled ovarian hyperstimulation for in vitro fertilization alters endometrial receptivity in humans: protocol effects", Biology of Reproduction, 2010, pp. 679-686, vol. 82.
Haouzi et al., "Transcriptome analysis reveals dialogues between human trophectoderm and endometrial cells during the implantation period", Human Reproduction, 2011, pp. 1440-1449, vol. 26, No. 6.
Chang et al., "Expression of steroid receptors, their cofactors, and aromatase in human luteinized granulosa cells after controlled ovarian hyperstimulation", Fertility & Sterility, Apr. 2005, pp. 1241-1247, vol. 83, no. Suppl. 1.
Diaz-Gimeno et al., "A genomic diagnostic tool for human endometrial receptivity based on the transcriptomic signature", Fertility and Sterility, Jan. 1, 2011, pp. 50-60, vol. 95, No. 1, Elsevier Science Inc, New York, NY.
Ouandagogo et al., "Human cumulus cells molecular signature in relation to oocyte nuclear maturity stage", PLOS One, Nov. 2011, pp. 1-6, vol. 6, No. 11.

* cited by examiner

*Primary Examiner* — Amanda Haney
(74) *Attorney, Agent, or Firm* — Whitham, Curtis & Cook, P.C.

(57) ABSTRACT

Disclosed herein are methods and kits for assessing the endometrial receptivity of a patient after controlled ovarian hyperstimulation. More particularly, provided herein is a method for assessing the endometrial receptivity of a patient after controlled ovarian hyperstimulation, comprising a step consisting of measuring the expression level of at least one gene selected from fifteen genes in an endometrial biopsy sample obtained from the patient wherein the genes are FGFBP1, MUC20, TMPRSS3, PRUNE2, HES2, MGST1, ERRFI1, EDN1, SLC17A7, MET, CPT1B, DCDC2, LRRC39, IL18RAP, and FOXP1.

1 Claim, 3 Drawing Sheets

Figure 1:
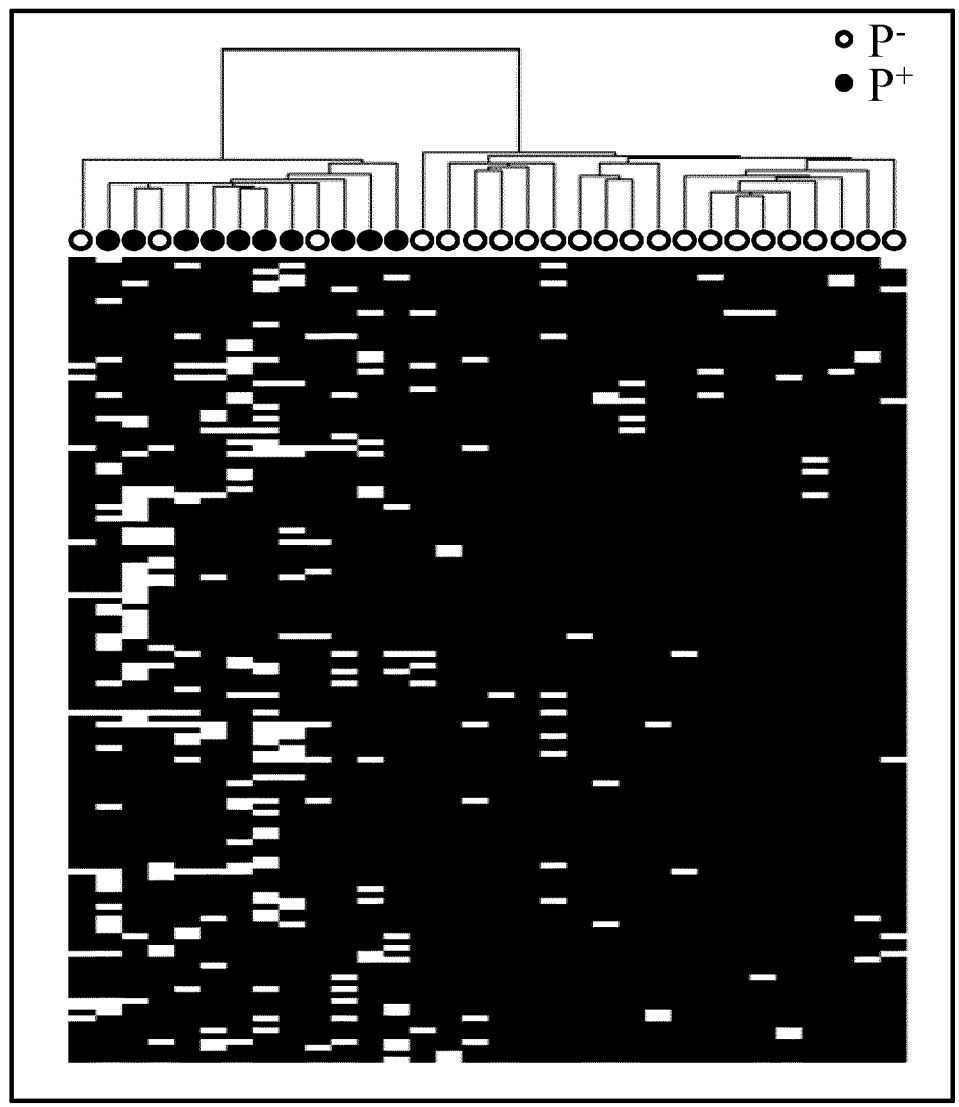

METHODS FOR ASSESSING ENDOMETRIAL RECEPTIVITY OF A PATIENT AFTER CONTROLLED OVARIAN HYPERSTIMULATION

CROSS REFERENCE TO RELATED APPLICATIONS

This application is a National Stage Application based on the International Application No. PCT/EP2012/070892 filed Oct. 22, 2012 which claims priority to European Application 11306364.8 filed Oct. 21, 2011.

FIELD OF THE INVENTION

The present invention relates to methods and kits for assessing the endometrial receptivity of a patient after controlled ovarian hyperstimulation.

BACKGROUND OF THE INVENTION

Despite many advances in assisted reproductive technology (ART), pregnancy rates are still low after controlled ovarian hyperstimulation (COH) and in vitro fertilization (IVF). Establishment and maintenance of pregnancy is a complex process which depends on several factors including successful implantation, a competent embryo, a receptive endometrium and a synchronized mother-embryo crosstalk. Identification of biomarkers according to the pregnancy outcome is a challenge to improve the clinical outcome under IVF conditions. With the emergence of new technologies like Omics, biomarkers as discovery tools that can be applied to IVF for the selection of competent embryos, the appreciation of endometrial receptivity and the synchronized dialogue between trophectoderm and endometrial cells have been identified (Assou et al., 2008, 2010; Hamel et al., 2008, 2010; Carson et al., 2002; Díaz-Gimeno et al., 2011; Domínguez et al., 2009; Haouzi et al., 2009a; Li et al., 2006; Mirkin et al., 2005; Riesewijk et al., 2003; Talbi et al., 2006; Haouzi et al., 2011). To date, only gene expression profile of follicular cells such as cumulus and granulosa cells have been correlated with pregnancy outcome (Assou et al., 2008, 2010; Hamel et al., 2008, 2010; Gebhardt et al., 2011; Assidi et al., 2011). In order to identify new biomarkers relate to implantation receptivity and pregnancy outcome, the inventors performed the gene expression profiles of human endometrium on oocyte retrieval day from normal young responder patients under controlled ovarian hyperstimulation.

There is no disclosure in the art of biomarkers of endometrial receptivity in patients under controlled ovarian hyperstimulation. However, there is a need to develop new methods for predicting endometrial receptivity outcome in patients after controlled ovarian hyperstimulation.

SUMMARY OF THE INVENTION

The present invention relates to a method for assessing the endometrial receptivity of a patient after controlled ovarian hyperstimulation, comprising a step consisting of measuring the expression level of at least one gene selected from fifteen genes in an endometrial biopsy sample obtained from said patient wherein said fifteen genes are FGFBP1, MUC20, TMPRSS3, PRUNE2, HES2, MGST1, ERRFI1, EDN1, SLC17A7, MET, CPT1B, DCDC2, LRRC39, IL18RAP, and FOXP1.

DETAILED DESCRIPTION OF THE INVENTION

The inventors aimed at identifying genes expressed in human endometrium on the oocyte collection day under controlled ovarian hyperstimulation that could be used as biomarkers of endometrial receptivity after controlled ovarian hyperstimulation.

A series of young (<36 years) normal responder patients (n=32), referred for IVF due to male infertility, underwent endometrial biopsies on the day of oocyte collection (36 hours after hCG administration, hCG+2) under controlled ovarian hyperstimulation. The mRNA extracted from endometrial biopsy samples were analyzed individually on affymetrix HG-U133 plus 2.0 GeneChip oligonucleotide microarrays. The differential gene expression profile according to ongoing pregnancy outcome (10 pregnant versus 22 non-pregnant patients) was evaluated with bioinformatics methods (SAM, Significant Analysis of Microarrays; fold change>1.2 and FDR<5%). Genes were analyzed using Ingenuity Pathway Analysis (IPA) software (Ingenuity Systems, Redwood City, Calif.).

A genetic imprint in endometrium on the day of oocyte retrieval associated with a positive pregnancy outcome was identified. This molecular signature comprised 124 genes (corresponding to 137 probe sets) which were all down-regulated in the positive pregnancy outcome group. Hierarchical clustering confirmed that this 124 genes list indeed 100% of endometrial samples associated with and without achieving pregnancy (FIG. 1).

Among genes whose down-expression is associated with pregnancy, the most overrepresented biological pathways were the HGF and FGF signaling. They included HGF (x-1.8, FDR<0.0001), FGF18 (x-1.8, FDR<0.0001), FGFBP1 (x-3.9, FDR<0.0001), and MET (x-2.1, FDR<0.0001). The top-fifteen most down-regulated genes have been selected (FGFBP1, MUC20, TMPRSS3, PRUNE2, HES2, MGST1, ERRFI1, EDN1, SLC17A7, MET, CPT1B, DCDC2, LRRC39, IL18RAP, FOXP1) and are proposed as prognostic value of endometrial receptivity after controlled ovarian hyperstimulation. As the endometrial biopsy is an easy procedure to perform on the oocyte collection day under controlled ovarian hyperstimulation, the method represents a novel strategy to improve the implantation and pregnancy rates of poor implanted patients.

Accordingly, the present invention relates to a method for assessing the endometrial receptivity of a patient after controlled ovarian hyperstimulation, comprising a step consisting of measuring the expression level of at least one gene selected from fifteen genes in an endometrial biopsy sample obtained from said patient wherein said fifteen genes are FGFBP1, MUC20, TMPRSS3, PRUNE2, HES2, MGST1, ERRFI1, EDN1, SLC17A7, MET, CPT1B, DCDC2, LRRC39, IL18RAP, and FOXP1.

As used herein the term "patient" refers to a mammalian female to which the present invention may be applied. Typically said mammal is a human (i.e a woman), but may concern other mammals such as primates, dogs, cats, pigs, sheep, cows.

The term "controlled ovarian hyperstimulation" or "COH" has it general meaning in the art and refers to the method for inducing a stimulated cycle for which a patient produces more than one oocyte. Typically COH is performed with a combination of GnRH agonist or antagonist protocols with either highly purified human menopausal gonadotrophin (hMG) or recombinant FSH.

As used herein the term "endometrial receptivity" is a period in which the endometrium acquires a functional status that allows blastocyst adhesion and that will lead to successful pregnancy.

In a particular embodiment the biopsy is performed during the stimulated cycle (the cycle after COH) and preferably on the day of oocyte collection (hCG+2).

In a particular embodiment, the expression level of 1, 2, 3, 4, 5, 6, 7, 8, 9, 10, 11, 12, 13, 14 or 15 genes is measured. Preferably, the expression level of the fifteen genes is measured.

All the genes pertaining to the invention are known per se, and are listed in the below Table A.

TABLE A

Set of predictive genes.

| Gene Symbol | Gene name | Gene ID |
|---|---|---|
| FGFBP1 | Fibroblast growth factor binding protein 1 | 9982 |
| MUC20 | Mucin 20, cell surface associated | 200958 |
| TMPRSS3 | Transmembrane protease, serine 3 | 64699 |
| PRUNE2 | Prune homolog 2 (*Drosophila*) | 158471 |
| HES2 | Hairyand enhancer of slip 2 (*Drosophila*) | 54626 |
| MGST1 | Microsomal glutathione S-transferase 1 | 4257 |
| ERRFI1 | ERBB receptor feedback inhibitor 1 | 54206 |
| EDN1 | Endothelin 1 | 1906 |
| SLC17A7 | Solute carrier family 17 (sodium-dependent inorganic phosphate cotransporter), member 7 | 57030 |
| MET | Met proto-oncogene (hepatocyte growth factor receptor) | 4233 |
| CPT1B | Carnitine palmito yltransferase 1B (muscle) | 1375 |
| DCDC2 | Double cortin domain containing 2 | 51473 |
| LRRC39 | Leucine rich repeat containing 39 | 127495 |
| IL18RAP | Interleukin 18 receptor accessory protein | 8807 |
| FOXP1 | Forkhead box P1 | 27086 |

Determination of the expression level of the genes as above described in Table A can be performed by a variety of techniques. Generally, the expression level as determined is a relative expression level.

More preferably, the determination comprises contacting the endometrial biopsy sample with selective reagents such as probes, primers or ligands, and thereby detecting the presence, or measuring the amount, of polypeptide or nucleic acids of interest originally in the endometrial biopsy sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the endometrial biopsy sample.

In a preferred embodiment, the expression level may be determined by determining the quantity of mRNA.

Methods for determining the quantity of mRNA are well known in the art. For example the nucleic acid contained in the endometrial biopsy sample is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total RNAs extracted from an endometrial biopsy samples and subjecting the RNAs to amplification and hybridization to specific probes, more particularly by means of a quantitative or semi-quantitative RT-PCR.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, an endometrial biopsy sample from a test patient, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210)

In this context, the invention further provides a DNA chip comprising a solid support which carries nucleic acids that are specific to the genes listed in table A.

Other methods for determining the expression level of said genes include the determination of the quantity of proteins encoded by said genes.

Such methods comprise contacting the endometrial biopsy sample with a binding partner capable of selectively interacting with a marker protein present in the endometrial biopsy sample. The binding partner is generally an antibody that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with an antibody against the protein to be tested. An endometrial biopsy sample containing or suspected of containing the marker protein is then added to the coated wells. After a period of incubation sufficient to allow the formation of antibody-antigen complexes, the plate (s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Alternatively an immunohistochemistry (IHC) method may be preferred. IHC specifically provides a method of detecting targets in the endometrial biopsy sample in situ. The overall cellular integrity of the endometrial biopsy sample is maintained in IHC, thus allowing detection of both the presence and location of the targets of interest. Typically a endometrial biopsy sample is fixed with formalin, embedded in paraffin and cut into sections for staining and subsequent inspection by light microscopy. Current methods of IHC use either direct labeling or secondary antibody-based or hapten-based labeling. Examples of known IHC systems include, for example, EnVision™ (DakoCytomation), Powervision(R) (Immunovision, Springdale, Ariz.), the NBA™ kit (Zymed Laboratories Inc., South San Francisco, Calif.), HistoFine(R) (Nichirei Corp, Tokyo, Japan).

In particular embodiment, a tissue section (i.e. endometrial biopsy sample) may be mounted on a slide or other support after incubation with antibodies directed against the proteins encoded by the genes of interest. Then, microscopic inspections in the sample mounted on a suitable solid support may be performed. For the production of photomicrographs, sections comprising endometrial biopsy sample may be mounted on a glass slide or other planar support, to highlight by selective staining the presence of the proteins of interest.

Therefore IHC endometrial biopsy samples may include, for instance: (a) preparations comprising endometrial cells (b) fixed and embedded said cells and (c) detecting the proteins of interest in said endometrial biopsy samples. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibodies, washing, applying secondary antibodies (optionally coupled to a suitable detectable label), washing, counter staining, and microscopic examination.

The method of the invention may further comprise a step consisting of comparing the expression level of the genes in the endometrial biopsy sample with a control sample, wherein detecting differential in the expression level of the genes between the endometrial biopsy sample and the control sample is indicative whether the endometrium is receptive or not. Typically, the control sample may consist in an endometrial biopsy sample obtained from a receptive endometrium or a non-receptive endometrium and preferably, an endometrial biopsy sample obtained from a non receptive endometrium. Typically, the level of expression of said gene(s) in a patient whom the endometrium is receptive is deemed to be lower ("down expression") than the control sample consisting of an endometrial biopsy sample obtained from a non receptive endometrium. For example, a down-expressed gene has a level of expression at least 1.5, at least 2, at least 2.5, at least 5, at least 7.5 or at least 10 times lower than the level of expression of said gene in a control sample.

In one embodiment, the method of the invention comprises the steps of measuring the expression level of 1, 2, 3, 4, 5, 6, 7, 8, 9, 10, 11, 12, 13, 14 or 15 genes of the invention in the endometrial biopsy sample obtained from a patient after controlled ovarian hyperstimulation, calculating a score, and comparing said score to a reference value.

In one embodiment, said reference value may be a score calculated in the endometrial biopsy samples of a negative control (an endometrial biopsy sample obtained from a non-receptive endometrium, non-pregancy patient) or a positive control (an endometrial biopsy sample obtained from a receptive endometrium, pregnancy patient).

In one embodiment, when the expression levels of at least 2 genes of the invention were measured, the score may be the mean or the average of the expression levels of all of the genes measured in the endometrial biopsy sample.

The inventors have thus demonstrated that controlled ovarian hyperstimulation (COH) can impact endometrial receptivity. Accordingly, the method of the invention opens new perspectives in ART, particularly in patients with multiple implantation failures. In this case, analysis of the endometrial profile could reveal a strongly altered profile during COH protocols, prompting the clinician to either adapt the IVF stimulation protocol or to perform embryo transfer later during a natural cycle. More particularly, when the receptiveness of the endometrium is seriously compromised by the COH protocol, fresh embryo replacement should be cancelled, the embryo (or oocyte) frozen and thawed embryo replacement should be performed under natural cycles.

The invention also relates to a kit for performing the methods as above described, wherein said kit comprises means for measuring the expression level of at least one gene selected from Table A.

The invention will be further illustrated by the following figures and examples. However, these examples and figures should not be interpreted in any way as limiting the scope of the present invention.

FIGURE

FIG. 1: The "pregnancy outcome" gene list delineates two groups of endometrial samples according the pregnancy outcome. $P^{-1}$, without pregnancy; $P^+$, with positive pregnancy.

Figure 2:
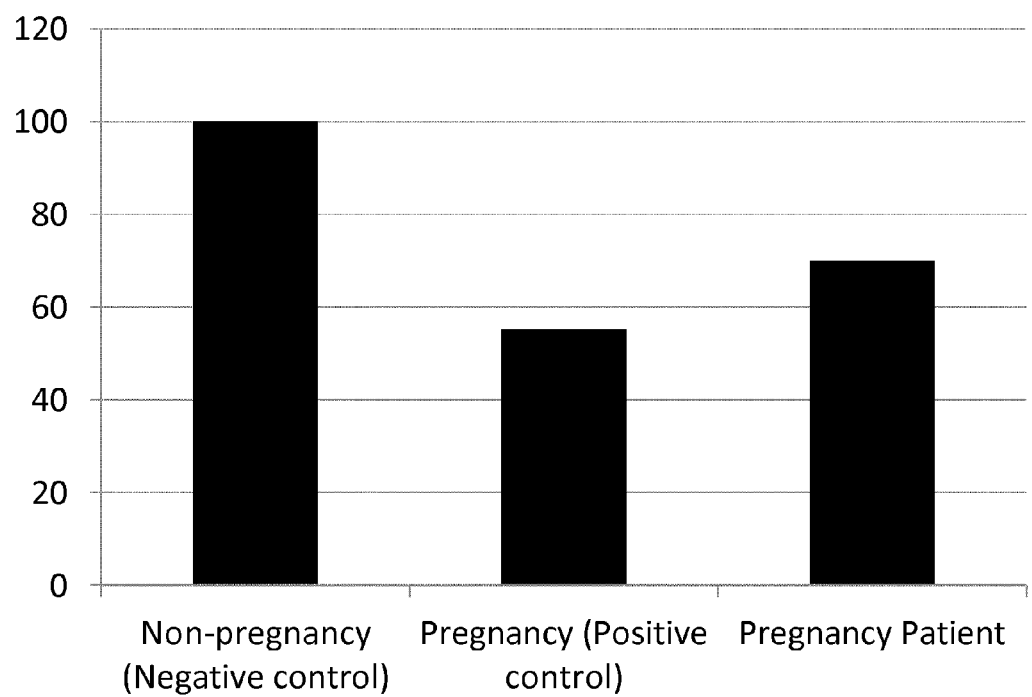

FIG. 2: Edometrial receptivity of a patient after controlled ovarian hyperstimulation. The endometrial biopsy sample was obtained the day of oocyte collection. Down-expression of the genes of the invention are indicative that the endometrium is non-receptive. The patient present a non-receptive endometrium and an unfavourable embryo transfer.

Figure 3:
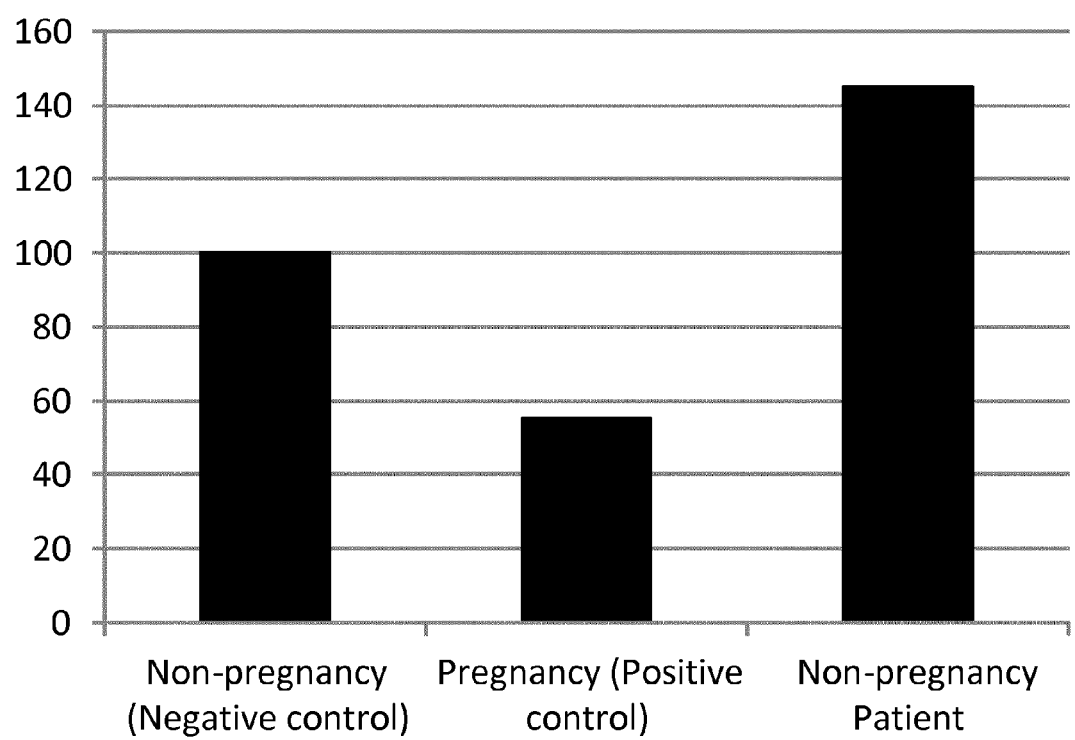

FIG. 3: Edometrial receptivity of a patient after controlled ovarian hyperstimulation. The endometrial biopsy sample was obtained the day of oocyte collection. Over-expression of the genes of the invention are indicative that the endometrium is receptive. The patient present a receptive endometrium and a favourable embryo transfer.

EXAMPLES

Example 1

Material & Methods

Patient characteristics and endometrial biopsy: This project has received institutional review board approval. The study population included 32 normal responder patients (normal serum FSH, LH and estradiol on day 3), age<36 years and referred for IVF due to male infertility. Patients had controlled ovarian stimulation with a combination of GnRH agonist long or antagonist protocols with either highly purified human menopausal gonadotrophin or recombinant FSH. After having collected the patient's informed consent, one endometrial biopsy was carried out in conditions of stimulated cycle and on the day of oocyte collection (hCG+2). Each biopsy was frozen at −80° C. in RLT RNA extraction buffer (RNeasy Mini kit, Qiagen, Valencia, Calif., USA).

Complementary RNA (cRNA) preparation and microarray hybridization: Total RNA (between 50 to 100 ng) was used to prepare twice amplified and labelled cRNA for hybridization with HG-U133 plus 2.0 arrays (Affymetrix™) as described in Haouzi et al. (2009). Each endometrial biopsy was processed individually on a DNA microarray chip.

Data Processing:

Scanned GeneChip images were processed using the AGCC (Affymetrix GeneChip Command Console) software. Microarray data were analyzed using the Affymetrix Expression Console software and normalization was performed with the MAS5 algorithm to obtain a detection call and an intensity value signal for each probe set.

Bioinformatics and in Silico Analyses:

The Significant Analysis of microarrays (SAM, Stanford University, USA, Tusher et al. 2001) was used to identify genes whose expression varied significantly between the two hCG+2 sample groups, pregnant (n=10) and non-pregnant (n=22). SAM provides mean or median fold change values (FC) and a false discovery rate (FDR) confidence percentage based on data permutation.

To compare profile expression of hCG+2 endometrial samples (n=32) from pregnant and non-pregnant groups, we performed a supervised classification with hierarchical clustering. Hierarchical clustering analysis based on the expression levels of varying probes were performed with the CLUSTER and TREEVIEW software packages.

Functional Annotations:

Selected gene lists were analyzed using Ingenuity Pathway Analysis (IPA) software (Ingenuity Systems, Redwood City, Calif.). Those genes with known gene symbols and their corresponding expression values were uploaded into the software. Each gene symbol was mapped to its corresponding gene object in the Ingenuity Pathways Knowledge Base. Networks of these genes were algorithmically generated based on their connectivity and assigned a score. The score is a numerical value used to rank networks according to how relevant they are to the genes in the input dataset but may not be an indication of the quality or significance of the network. The score takes into account the number of focus genes in the network and the size of the network to approximate how relevant this network is to the original list of focus genes. The network identified is then presented as a graph indicating the molecular relationships between genes/gene products. Genes are represented as nodes, and the biological relationship between two nodes is represented as an edge (line).

Results

Distinct hCG+2 Gene Expression Profile in Endometrium Between Pregnant and Non-Pregnant Patients Selection using a variation coefficient (≥40%) and the Absent/Present "detection call" (presence in at least 1 sample) between hCG+2 endometrial samples from pregnant and non-pregnant patients was first performed, delineating 14,378 probe sets. Then, we performed a SAM analysis between the two groups: 137 probe sets corresponding to 124 genes were significantly down-regulated in the pregnant group compared with the non-pregnant group. Supervised clustering with these 124 genes clearly separated the two endometrial groups (FIG. 1). The fifteen most down-regulated genes are listed in the Table B.

Two Major Signaling Pathways Differ Between Pregnant and Non-Pregnant Endometrial Groups Among genes whose down-expression is associated with pregnancy, the most overrepresented biological pathways were the HGF and FGF signaling. They included HGF (x-1.8, FDR<0.0001), FGF18 (x-1.8, FDR<0.0001), FGFBP1 (x-3.9, FDR<0.0001), and MET (x-2.1, FDR<0.0001).

TABLE B

Set of predictive genes.

| Gene Symbol | Gene Name | Gene ID | Fold Change | q-value (%) |
|---|---|---|---|---|
| FGFBP1 | Fibroblast growth factor binding protein 1 | 9982 | −3,888 | 0 |
| MUC20 | Mucin 20, cell surface associated | 200958 | −2,599 | 0 |
| TMPRSS3 | Transmembrane protease, serine 3 | 64699 | −2,411 | 0 |
| PRUNE2 | Prune homolog 2 (Drosophila) | 158471 | −2,401 | 0 |
| HES2 | Hairy and enhancer of split 2 (Drosophila) | 54626 | −2,360 | 0 |
| MGST1 | Microsomal glutathione S-transferase 1 | 4257 | −2,354 | 0 |
| ERRFI1 | ERBB receptor feedback inhibitor 1 | 54206 | −2,322 | 0 |
| EDN1 | Endothelin 1 | 1906 | −2,245 | 0 |
| SLC17A7 | Solute carrier family 17 (sodium-dependent inorganic phosphate cotransporter), member 7 | 57030 | −2,158 | 0 |
| MET | Met proto-oncogene (hepatocyte growth factor receptor) | 4233 | −2,124 | 0 |
| CPT1B | Carnitine palmitoyltransferase 1B (muscle) | 1375 | −2,046 | 0 |
| DCDC2 | Double cortin domain containing 2 | 51473 | −2,028 | 0 |
| LRRC39 | Leucine rich repeat containing 39 | 127495 | −2,025 | 0 |
| IL18RAP | Interleukin 18 receptor accessory protein | 8807 | −2,019 | 0 |
| FOXP1 | Forkhead box P1 | 27086 | −1,970 | 0 |

Example 2

The inventors have conducted prospective studies to validate the relevance of the diagnostic tests according to the invention for assessing the endometrial receptivity of a patient after controlled ovarian hyperstimulation.

The study population included all patients under COS undergoing IVF/ICSI procedures. The method according to the invention has been validated by inventors using quantitative RT-PCR in an endometrial biopsy sample obtained the day of oocyte collection.

The expression level of the 15 genes of the invention in the endometrial biopsy sample of the patients was measured, the mean of the expression level of the 15 genes of the invention was calculated and compared to the expression level of said genes in the endometrial biopsy samples of a negative control (non-pregancy patient) and a positive control (pregnancy patient).

The results demonstrated that down expression of the genes of the invention are indicative that the endometrium is receptive (FIG. 2) and over expression of the genes of the invention are indicative that the endometrium is non-receptive (FIG. 3). The genes of the invention present a prognostic value of endometrial receptivity after controlled ovarian hyperstimulation.

REFERENCES

Throughout this application, various references describe the state of the art to which this invention pertains. The disclosures of these references are hereby incorporated by reference into the present disclosure.

Assidi M, Montag M, Van der Ven K, Sirard M A. Biomarkers of human oocyte developmental competence expressed in cumulus cells before ICSI: a preliminary study. J Assist Reprod Genet. 2011; 28(2):173-88.

Assou S, Haouzi D, De Vos J, Hamamah S. Human cumulus cells as biomarkers for embryo and pregnancy outcomes. Mol Hum Reprod. 2010; 16(8):531-8.

Assou S, Haouzi D, Mahmoud K, Aouacheria A, Guillemin Y, Pantesco V, Rème T, Dechaud H, De Vos J, Hamamah S. A non-invasive test for assessing embryo potential by gene expression profiles of human cumulus cells: a proof of concept study. Mol Hum Reprod. 2008; 14(12):711-9.

Carson D D, Lagow E, Thathiah A, Al-Shami R, Farach-Carson M C, Vernon M, Yuan L, Fritz M A, Lessey B, 2002. Changes in gene expression during the early to mid-luteal (receptive phase) transition in human endometrium detected by high-density microarray screening. Mol. Hum. Reprod. 8, 871-879.

Díaz-Gimeno P, Horcajadas J A, Martínez-Conejero J A, Esteban F J, Alamà P, Pellicer A, Simón C, 2011. A genomic diagnostic tool for human endometrial receptivity based on the transcriptomic signature. Fertil. Steril. 95(1), 50-60, 60.e1-15.

Domínguez F, Garrido-Gómez T, López J A, Camafeita E, Quiñonero A, Pellicer A, Simón C, 2009. Proteomic analysis of the human receptive versus non-receptive endometrium using differential in-gel electrophoresis and MALDI-MS unveils stathmin 1 and annexin A2 as differentially regulated. Hum. Reprod. 24, 2607-2617.

Gebhardt K M, Feil D K, Dunning K R, Lane M, Russell D L. Human cumulus cell gene expression as a biomarker of pregnancy outcome after single embryo transfer. Fertil Steril. 2011; 96(1):47-52.e2.

Hamel M, Dufort I, Robert C, Gravel C, Leveille M C, Leader A, Sirard M A. Identification of differentially expressed markers in human follicular cells associated with competent oocytes. Hum Reprod. 2008; 23(5):1118-27.

Hamel M, Dufort I, Robert C, Léveillé M C, Leader A, Sirard M A. Genomic assessment of follicular marker genes as pregnancy predictors for human IVF. Mol Hum Reprod. 2010; 16(2):87-96.

Haouzi D, Dechaud H, Assou S, Monzo C, de Vos J, Hamamah S. Transcriptome analysis reveals dialogues between human trophectoderm and endometrial cells during the implantation period. Hum Reprod. 2011; 26(6):1440-9.

Haouzi D, Mahmoud K, Fourar M, Bendhaou K, Dechaud H, De Vos J, Rème T, Dewailly D, Hamamah S, 2009. Identification of new biomarkers of human endometrial receptivity in the natural cycle. Hum. Reprod. 24, 198-205.

Li J, Tan Z, Li M T, Liu Y L, Liu Q, Gu X F, Zhou J Z, Zhuang G L, 2006. [Study of altered expression of annexin IV and human endometrial receptivity]. Zhonghua Fu Chan Ke Za Zhi 41, 803-805.

Mirkin S, Arslan M, Churikov D, Corica A, Diaz J I, Williams S, Bocca S, Oehninger S, 2005. In search of candidate genes critically expressed in the human endometrium during the window of implantation. Hum. Reprod. 20, 2104-2117.

Riesewijk A, Martin J, van Os R, Horcajadas J A, Polman J, Pellicer A, Mosselman S, Simón C, 2003. Gene expression profiling of human endometrial receptivity on days LH+2 versus LH+7 by microarray technology. Mol. Hum. Reprod. 9, 253-264.

Talbi S, Hamilton A E, Vo K C, Tulac S, Overgaard M T, Dosiou C, Le Shay N, Nezhat C N, Kempson R, Lessey B A, Nayak N R, Giudice L C, 2006. Molecular phenotyping of human endometrium distinguishes menstrual cycle phases and underlying biological processes in normo-ovulatory women. Endocrinology 147, 1097-1121.

Tusher V G, Tibshirani R, Chu G. Significance analysis of microarrays applied to the ionizing radiation response. Proc Natl Acad Sci USA 2001:98; 5116-5121.

The invention claimed is:

1. A method for assessing the endometrium of and implanting an embryo in a woman undergoing in vitro fertilization (IVF) after controlled ovarian hyperstimulation (COH), comprising the steps of:
   a) obtaining an endometrial biopsy sample from said woman on the day of oocyte collection (hCG+2) of a stimulated cycle;
   b) measuring, in said endometrial biopsy sample, the mRNA level of each of the following fifteen genes: FGFBP1, MUC20, TMPRSS3, PRUNE2, HES2, MGST1, ERRFI1, EDN1, SLC17A7, MET, CPT1B, DCDC2, LRRC39, IL18RAP, and FOXP1;
   c1) comparing the mRNA level of each of the fifteen genes in the endometrial biopsy sample with control mRNA levels of said each gene from an endometrial biopsy sample obtained on the day of oocyte collection (hCG+2) from a patient that did not become pregnant after COH; and
   determining that the mRNA level of at least one gene is down regulated compared to the control thereby assessing the endometrium of the woman as being receptive; or
   c2) comparing the mRNA level of each of the fifteen genes in the endometrial biopsy sample with control mRNA levels of said each gene from an endometrial biopsy sample obtained on the day of oocyte collection (hCG+2) from a patient that became pregnant after COH; and
   determining that the mRNA levels of the fifteen genes in the endometrial biopsy sample are not down or up regulated compared to the control mRNA levels of said fifteen genes thereby assessing the endometrium of the woman as being receptive; and
   d) implanting an embryo in said woman having a receptive endometrium as determined in step c1) or c2).

* * * * *